United States Patent [19]

Haubs et al.

[11] Patent Number: 5,710,241
[45] Date of Patent: Jan. 20, 1998

[54] MONOANHYDRIDE COMPOUNDS, METHOD OF MAKING SAME AND REACTION PRODUCTS THEREOF

[75] Inventors: Michael Haubs, Bad Kreuznach, Germany; Paul Foley, Oldwick; Dominick L. Cangiano, Neshanic, both of N.J.

[73] Assignee: Hoechst Celanese Corp., Summit, N.J.

[21] Appl. No.: 205,054

[22] Filed: Mar. 2, 1994

[51] Int. Cl.$^6$ .................................................. C08G 69/26
[52] U.S. Cl. ........................ 528/353; 525/436; 540/450; 549/245
[58] Field of Search ................... 528/353; 549/245; 540/450

[56] References Cited

U.S. PATENT DOCUMENTS

| | | | |
|---|---|---|---|
| 4,374,076 | 2/1983 | Stephan et al. | 264/19 |
| 4,479,930 | 10/1984 | Hnatowich | 424/1.1 |
| 4,742,153 | 5/1988 | Sutton, Jr. | 528/353 |
| 5,110,879 | 5/1992 | Chung et al. | 525/432 |

FOREIGN PATENT DOCUMENTS

| | | | |
|---|---|---|---|
| 2000824 | 12/1969 | France . | |
| 63-037118 | 2/1988 | Japan . | |
| 63-165427 | 7/1988 | Japan . | |

OTHER PUBLICATIONS

Kallitsis, J. et al., "Attempts to Synthesize Networks From Rigid-Rod Oligomers". Makromolekulare Chemie Pre--Print Aug., 1991.

Kim et al., "Hyperbranched Polyphenylenes", Macromolecules, vol. 25, No. 21, ACS, Oct. 1992.

Lemay et al., "Low Density Microcellular Materials", Mrs Bulletin, Dec., 1990.

*Primary Examiner*—Ana Woodward
*Attorney, Agent, or Firm*—Michael W. Ferrell

[57] ABSTRACT

The present invention relates to monoanhydride monomer compounds, methods of making such compounds and reaction products of the monoanhydride-diacid compounds with other monomers. The inventive monomer compounds exhibit selective reactivity, that is, the dianhydride locus is substantially more reactive towards amines than the diacid locus making it possible to sequentially synthesize a new class of materials suitable for membranes, catalytic substrates or any speciality material required for advanced applications.

5 Claims, No Drawings

MONOANHYDRIDE COMPOUNDS, METHOD OF MAKING SAME AND REACTION PRODUCTS THEREOF

CROSS REFERENCE TO RELATED APPLICATION

The present invention is related to the invention described in a copending United States Patent Application entitled Macrocyclic Imide Compounds, U.S. Ser. No. 08/205,056, now abandoned filed of even date herewith. The disclosure of this related case is incorporated herein by reference as if fully set forth below.

TECHNICAL FIELD

The present invention relates generally to monoanhydride compounds and in particular embodiments to compounds useful for producing rigid-rod networked polyimides.

BACKGROUND ART

Branched polymers with networked microstructures are known to be useful for making aerogels and other materials where a high degree of crosslinking is typical. The hydrolysis and condensation of tetraalkoxy silanes is the principle synthetic route for the formation of silica aerogels or xerogels. Major variables in the polymerization process include the type of alkoxy silane, solution pH, and the $H_2O/Si$ ratio. Like organic materials have been synthesized from resorcinol with formaldehyde or from melamine with formaldehyde. See LeMay et. al. Low Density Microcellular Materials, pp. 30 et seq., MRS Bulletin, December 1990.

Highly branched polymers are of interest generally due to their potential for molecular composites, rheology control agents as well as multifunctional macromonomers for specialized materials, such as those useful in connection with membranes. Illustrative of such polymers include hyperbranched polyphenylenes as reported by Kim and Webster, Macromolecules, Volume 25, No. 21, Oct. 12, 1992 pp. 5562. Other polymers of the rigid-rod class have been reported by Kallitsis et al. of the Max Planck Institute, Mainz Germany.

A major obstacle to the general use of polymers with well-defined branched substructures has been the inability to control molecular structure and resultant properties at a reasonably low cost with high selectivity. It has been made possible by the present invention to produce branched structures with highly selective polyimide chemistry.

SUMMARY OF INVENTION

The present invention relates generally to monoanhydride compounds prepared from dianhydride compounds by way of partial hydrolysis of the dianhydride. The unique anhydride-diacid compounds exhibit a pair of reactive sites with disparate reactivities toward amine compounds, making it possible to selectively synthesize a wide variety of compounds with a branched or sequenced structure as needed or desired. In further aspects of the invention there are provided methods of making particular copolymers as well as films formed of the inventive reaction products.

DETAILED DESCRIPTION

The invention is described in detail below with reference to specific examples which are provided for purposes of illustration only. As one of skill in the art will readily appreciate, it is possible in accordance with the present invention to synthesize strictly alternating sequenced copolymers or to provide a polymeric material with the desired degree of branching or networking by applying kinetic theory developed by Flory and others. Likewise, while mixtures of dipolar aprotic organic solvents are the preferred medium in which to prepare the inventive monoanhydride compounds, it is possible to use solvents such as tetrahydrofuran (THF) within the scope of the present invention. So also, while it is desirable generally to convert most of the dianhydride compound employed to the corresponding monoanhydride, it is possible to convert substantial amounts of dianhydride to the corresponding tetra-acid which will not interfere with subsequent reactions which are selective to anhydride moieties.

There is provided in a first aspect of the present invention a method of preparing a monoanhydride from an aromatic dianhydride compound including the steps of: (a) dissolving an aromatic dianhydride in an organic solvent medium to prepare a solution; (b) adding water to the solution; and (c) maintaining the solution under conditions and for a time sufficient to convert a substantial portion of the dianhydride to the corresponding monoanhydride. In the most general sense, at least 10% of the dianhydride is converted to monohydride form, 50% or more being typical and over 80% being preferable. In most cases it is preferred to maintain the solution below about 40° C. during the dianhydride conversion process. Other temperatures may include less than about 95° C., 75° C., 65° C. or 55° C. depending upon the desired results and overall process.

Typically, the aromatic dianhydride includes the structural unit:

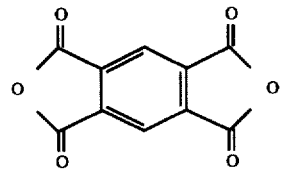

The organic solvent medium is typically a dipolar aprotic organic solvent, preferably selected from the group consisting of 1-methyl-2-pyrrolidinone, N,N-dimethylacetamide, N,N-dimethylformamide, dimethylsulfoxide and mixtures thereof. Most preferably, the organic solvent medium is from about forty to about sixty volume per cent of a first dipolar aprotic solvent and from about forty to about sixty per cent of a second dipolar aprotic solvent. In a surprisingly effective embodiment, the first dipolar aprotic solvent is 1-methyl-2-pyrrolidinone and the second dipolar aprotic solvent is N,N-dimethylacetamide.

The temperature of the solution may be maintained below about 30° C. and above about 0° C. for an initial period of up to about 4 hours and subsequently maintained at a temperature below about 0° C. for a second period of at least about 2 hours. The amount of water employed is in a stoichiometric ratio from about 1:1 to about 1.4:1 moles water/per mole of dianhydride.

Another aspect of the invention is a compound including the structural unit:

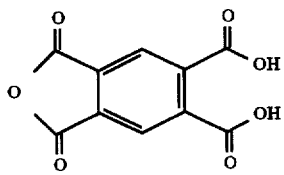

which may be substituted or unsubstituted such as having the formula:

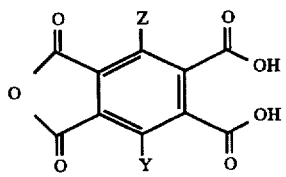

where Z and Y are the same or different and are selected from the group consisting of hydrogen, bromine, chlorine, OR, OCR, fluorine, nitro, $C_1$–$C_{18}$ alkyl, SR, NRR$^1$, SO$_x$R$^2$, COOR where X is 1,2 OR 3, R$^2$ is H, $C_1$–$C_{18}$ alkyl, NH$_2$ and R$^1$ is $C_1$–$C_{18}$ alkyl, COR and R is hydrogen, $C_1$–$C_{18}$ alkyl, $C_1$–$C_{18}$ alkenyl.

In a further aspect of the invention there is provided method of preparing a sequenced imide-anhydride reaction product including the steps in combination: (a) preparing a reaction mixture including a monoanhydride-diacid compound as the predominant anhydride component; (b) reacting the monoanhydride-diacid with a second compound having at least one primary amine functionality to form an amic acid-diacid intermediate; and (c) dehydrating the intermediate to form an imide-anhydride compound. Typically, the monoanhydride-diacid compound includes the structural unit:

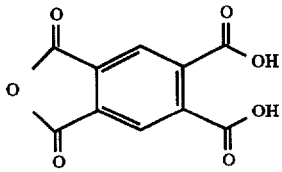

The second compound may be of the structure:

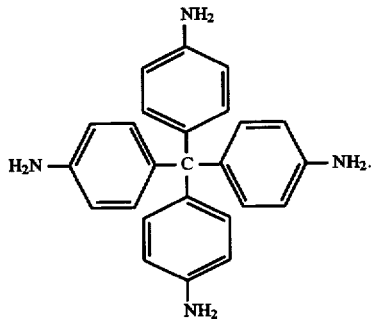

In a still further aspect of the invention there is disclosed imide-anhydride reaction products of a compound including the monoanhydride structural unit:

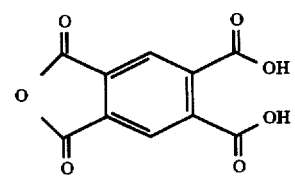

with at least a second compound having at least one primary amine functionalities.

Again, the second compound may be of the formula

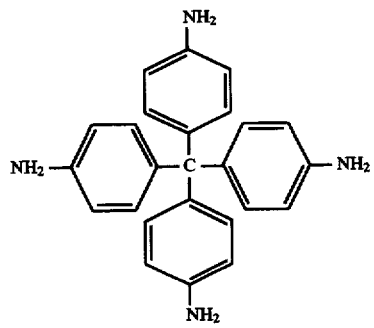

A sequenced polyimide may be prepared in accordance with the invention by: (a) preparing a reaction mixture including a monoanhydride-diacid compound as the predominant anhydride component; (b) reacting the monoanhydride-diacid with a second compound having at least one primary amine functionality to form an amic acid-diacid intermediate,(c) dehydrating the intermediate to from an imide-anhydride compound; and (d) reacting the imide-anhydride with at least a third primary amine, optionally with a reaction mixture of a diamine and a monoamine. The second compound may be a tetraamine.

Polymers according to the invention may have a second polymer blended therewith as will be apparent from the examples hereinafter provided. Polymer films including a polymer of the present invention are particularly useful as membranes or other articles of manufacture.

EXAMPLE 1. PARTIAL HYDROLYSIS OF PYROMELLETIC DIANHYDRIDE (PMDA)

26 g (0.12 mol) of PMDA are dissolved in 200 ml of a 1:1 mixture of 1-methyl-2-pyrrolidinone (NMP) and N,N-Dimethylacetamide (DMAc) at 25 C with stirring. To the clear solution is added 2.80 g (0.16 mol) of water in 40 ml of NMP. The temperature of the reaction mixture is kept at 25 C for 15 minutes with cooling. The temperature is then lowered by 5 C every 15 min. After 1 h (T=5 C) the flask is put into an ice bath and kept at −10 C for 4 h. At that point the reaction mixture typically consists of 86–87% pyromelletic monoanhydride (PMMA), 2–3% PMDA and 10–12% of pyromelletic acid (PMA). As the PMA does not react with amines it need not be separated and the mixture is ready for use (it is possible to determine the composition of the mixture by 1H-NMR of the nondeuterated reaction mixture; PMDA, PMMA and PMA give singlets at 8.82 ppm, 8.34 ppm and 8.07 ppm respectively).

EXAMPLE 2. REACTION OF PYROMELLETIC MONOANHYDRIDE WITH TETRAKIS (4-AMINOPHENYL) METHANE (TAPM)

TAPM was prepared according to literature procedures (F. A. Neugebauer et.al., Chem. Ber. 109, 2389–94 (1976). 8.4 g (0.022 mol) of TAPM are added to the cold mixture of Example 1 with stirring. 5 min after the solid is completely dissolved, 38 g (0.41 mol) of 3-picoline is added followed by addition of 35 g (0.34 mol) of acetic anhydride 3 min later. The solution is kept below 30 C. After about 1 h the first crystalline precipitate appears. The solution is allowed to stand overnight, filtered and washed with some NMP (containing 5% acidic anhydride) and with 40 ml of toluene. It is then dried in a vacuum oven at 100 C for 14 h with nitrogen bleed. The yield is 22 g. The structure of this compound was confirmed by 1H-NMR in DMSO-d6. It shows 2 singlets at 8.54 ppm and 7.56 ppm respectively.

The intensity ratio was 1:2. FD-mass spectra of a NMP dissolved sample gave the M-NQ$^\oplus$ peak at 1275.

EXAMPLE 3. PREPARATION OF HIGHLY BRANCHED RIGID ROD POLYIMIDE 1.12 g (0.95 mmol) Tetraanhydride of Example 2 (which has been dried at 200 C under nitrogen for 24 h) are dissolved in 20 ml of dry NMP with stirring and gentle heating to about 50 C. The clear solution is then cooled to about 5 C. A solution of 0.65 g (1.94 mmol) 4-tritylaniline and 0.11 g (1.02 mmol) p-phenylenediamine in 20 ml of dry NMP is added dropwise into the vortex of the well stirred solution until the solution turns viscous. The remaining anhydride groups are terminated with 0.05 g of 4-tritylaniline. The resulting highly branched polymer is imidized with 1 g of 3-picoline and 0.7 g of acetic anhydride over a period of 24 h. Even after complete imidisation the polymer stays soluble.

A part of the solution is cast on a glass plate and the solvent evaporated at 70 C under nitrogen. The resulting transparent film can be lifted under water but is quite brittle. The mechanical properties are improved by blending with other polymers (see Example 5.).

EXAMPLE 4.: PREPARATION OF A HIGHLY BRANCHED POLYIMIDE WITH MACROCYCLE SUBSTRUCTURES

The preparation from example 3 is repeated except that 0.2 g (1.02 mmol) of oxydianiline is used instead of 0.11 g of p-phenylendiamine. Films of the imidized polymer had much improved mechanical properties.

EXAMPLE 5. PREPARATION OF A BLEND FROM POLYARAMIDE WITH HIGHLY BRANCHED POLYIMIDE

The solution from example 3 was mixed with a 10% solution of a polyaramide prepared by the condensation of 4,4'-diaminophenyl-sulfone and terephthaloyl-chloride. The clear solution was cast on a glass plate with a doctors blade and the solvent evaporated at 80 C under nitrogen. The clear film lifted from the glass plate under water had good mechanical properties.

What is claimed:

1. A method of preparing an imide-anhydride compound comprising:

(a) selectively hydrolyzing an aromatic dianhydride in an organic solvent medium with an amount of water sufficient and under conditions effective to convert at least 50% of said aromatic dianhydride to the corresponding monoanhydride-diacid;

(b) reacting the monoanhydride-diacid medium of step (a) above with a second compound having at least one primary amine functionality to form an amic acid-diacid intermediate; and (c) dehydrating said intermediate to form an imide-anhydride compound.

2. The method according to claim 1, wherein said monoanhydride-diacid compound is of the structural formula:

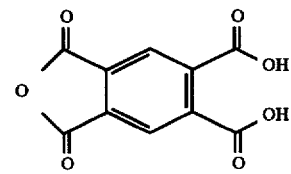

3. The method according to claim 1, wherein said second compound is

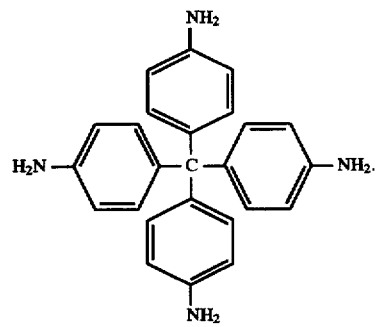

4. An imide-anyhride compound of an anhydride reactant having as its predominent anhydride component a monoanhydride-diacid of the structural formula:

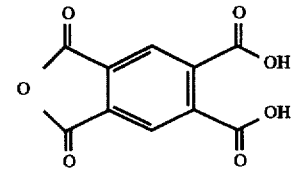

with at least a second compound having at least one primary amine functionality.

5. The reaction product according to claim 4, wherein said second compound is

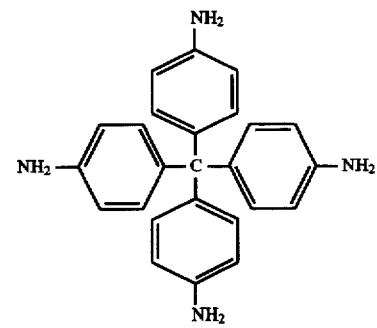

\* \* \* \* \*